United States Patent
Okumura et al.

(10) Patent No.: US 6,192,269 B1
(45) Date of Patent: Feb. 20, 2001

(54) OPHTHALMOLOGICAL MEASUREMENT APPARATUS

(75) Inventors: Toshiaki Okumura, Yokohama; Shinya Tanaka, Tokyo; Yasuyuki Numajiri, Kawasaki; Shigeaki Ono, Utsunomiya; Tomoyuki Iwanaga, Yokohama, all of (JP)

(73) Assignee: Canon Kabushiki Kaisha, Tokyo (JP)

( * ) Notice: Under 35 U.S.C. 154(b), the term of this patent shall be extended for 0 days.

(21) Appl. No.: 08/922,568

(22) Filed: Sep. 3, 1997

(30) Foreign Application Priority Data

Sep. 6, 1996 (JP) .................................................. 8-257563

(51) Int. Cl.[7] .................................................. A61B 5/00
(52) U.S. Cl. .......................................... 600/479; 600/504
(58) Field of Search .................................. 600/504, 558, 600/479, 564; 351/221, 205, 211, 210, 206; 356/28.5, 28

(56) References Cited

U.S. PATENT DOCUMENTS

| | | | |
|---|---|---|---|
| 5,031,632 | * | 7/1991 | Watanabe .............................. 128/691 |
| 5,633,695 | * | 5/1997 | Feke et al. ............................ 351/221 |
| 5,935,076 | * | 8/1999 | Smith et al. .......................... 600/479 |

* cited by examiner

Primary Examiner—Marvin M. Lateef
Assistant Examiner—Eleni Mantis Mercader
(74) Attorney, Agent, or Firm—Fitzpatrick, Cella, Harper & Scinto

(57) ABSTRACT

An ophthalmological measurement apparatus for measuring bloodstream velocity in an fundus blood vessel in an eye to be measured including a measurement system for measuring the bloodstream velocity in the fundus blood vessel, an input block for inputting information relating to the fundus blood vessel as an object to be measured by the measurement system, and a control block for selecting the measurement conditions and computation conditions of the measurement system, based on the information input by the input block.

18 Claims, 11 Drawing Sheets

FIG. 15

MEASUREMENT SCREEN

ID : Canon
Date : 1996.06.28

| Eye | Position | Time | Velocity (cm/sec) | Flow (ul/min) | |
|-----|----------|-------|-------------------|---------------|---|
| Right | Artery | 13:00 | ×××.×× | △△.△△ | |
| Right | Artery | 13:03 | ×××.×× | △△.△△ | * |
| Left | Artery | 13:05 | ×××.×× | △△.△△ | |
| Average | | | ×××.×× | △△.△△ | |

* : LESS RELIABLE

OPHTHALMOLOGICAL MEASUREMENT APPARATUS

BACKGROUND OF THE INVENTION

1. Field of the Invention

The present invention relates to an ophthalmological measurement apparatus for use in a medical institution, such as an ophthalmological clinic, which examines the fundus of a subject's eyes.

2. Description of the Related Art (1) A laser doppler flowmeter is a known ophthalmological measurement apparatus for measuring the velocity of a bloodstream in a blood vessel in the fundus of a subject's eyes. The fundus blood flowmeter directs a laser on an arbitrary blood vessel in the fundus of the subject's eyes, and detects a doppler shift of the laser light reflected from the bloodstream within the blood vessel. During measurement, the flowmeter keeps track of the same blood vessel to direct the laser light to the same blood vessel even when the eyeballs move. Photodetectors receive an interference signal between the doppler shift component of the reflected light from the bloodstream and the light from the sill vessel wall and the signal is frequency analyzed to determine a doppler shift frequency. Let $\Delta f \max 1$ and $\Delta f \max 2$ represent maximum doppler shift frequencies of the received signals from the two photodetectors, let represent the wavelength of the laser, let n represent a refractive index of a measurement point, let $\alpha$ represent an angle made between two receiving optical axes within the eye, and let $\beta$ represent an angle between a plane of the two receiving optical axes within the eye and the velocity vector of the bloodstream. The blood stream velocity (maximum velocity Vmax) is quantitatively determined by the following equation.

$$V\max = \{\lambda/(n \cdot \alpha)\} \cdot ||\Delta f \max 1| - |\Delta f \max 2||/\cos \beta \quad (1)$$

By making measurements from two directions in this way, the directional factors of the measurement lights cancel each other out. The bloodstream in an arbitrary point in the fundus is thus measured. By making the direction of the velocity vector coincide with the line where the fundus intersects the plane in which the two receiving optical axes lie, thus to make $\beta=0°$, namely $\cos \beta=1$, a true maximum blood stream velocity is measured.

(2) The maximum doppler shift $\Delta f \max$ is expressed as $|\Delta f \max|$ with its sign information dropped. When the bloodstream velocity is measured at different blood vessels in the fundus, the maximum frequency shifts $\Delta f \max 1$, $\Delta f \max 2$ may take three combinations of signs: both positive, both negative, and one positive and the other negative. As understood from Equation (1), determining the maximum bloodstream velocity Vmax becomes impossible, depending on the region of measurement. To resolve this problem, two points of incidence of light are set up at two direction to a spot image on the pupil, and maximum frequency shifts $|\Delta f \max 1|$, $|\Delta f \max 2|$, $|\Delta f \max 1'|$, and $|\Delta f \max 2'|$ are determined from the optical paths from the spot image, and the maximum bloodstream velocities Vmax and Vmax' are thus determined. By comparing the two maximum bloodstream velocities Vmax and Vmax', a proper angle of incidence of a light beam to determine a true maximum velocity is determined. Based on this information, the optical paths are selectively switched and an actual measurement is performed.

From the clinical standpoint, it is quite useful to observe changes in the subject's eyes with time. To fix the same region on the same blood vessel at the next time, a fundus image is recorded in a video cassette recorder or a video printer during a fundus bloodstream measurement, and the same region is visually determined referring to the measurement point position in the fundus image next time.

(a) In the conventional technique (1), however, the bloodstream velocity changes periodically in an artery in synchronization with the heart beat cycle of contraction and expansion. A measurement of at least one period is required on an artery while a measurement of short time is sufficient on a vein because of no substantial velocity change therewithin. Conventional measurements are performed without paying attention to the difference between the artery and the vein. A long measurement time, set for artery measurements, is too long for vein measurements. A subject is advised against blinking throughout the time. The fundus of the subject's eye are thus subject to a higher dose of light exposure than actually required.

Fast Fourier Transform (FFT) is typically used in the frequency analysis of doppler shift signals. To enhance the resolution of the frequency, a large quantity of time-series data is needed. The artery changes periodically, causing the bloodstream velocity to sharply rise at each contraction phase of the heart. If an excessively large quantity of data is used in the frequency analysis, velocity variations of interest will be obscured. On the other hand, the vein is practically subject to no such periodic velocity variations, and the use of a great deal of time-series data results in an increase in the frequency resolution in frequency analysis. In frequency analysis, consideration has to be given to acquiring data over a duration of time during which the velocity variations of interest in the artery are not obscured.

(b) In the conventional technique (2), a received signal may be affected by noise when the subject's eyes suffer from cataracts or when an eyelash is in the way during measurement. As a result, an accurate measurement will not be obtained in the determination of $\Delta f \max 1$ and $\Delta f \max 2$. From a cursory check, one cannot tell whether the measurements contain unwanted noise components possibly arising from cataracts or eyelashes, and thus one cannot determine whether the measurements are a true fundus bloodstream velocity. Since test personnel possibly observe the cataracts or eyelashes in the subject's eyes during a measurement, they may record that fact as reference information. The test personnel, however, are likely to forget recording in the course of busy measurement work.

Any particular manual work intervention, if introduced in the determination of the region of measurement, will increase error factors and decrease repeatability in measurement. The measurement work itself will be complicated and waste a lot of time. The region of measurement may be determined by observing and recording the fundus image and measurement spot using a CCD camera and by measuring the images. Such a measurement requires a complex and costly system.

SUMMARY OF THE INVENTION

It is a first object of the present invention to provide an ophthalmological measurement apparatus that resolves the problem discussed in paragraph (a) above and selects optimum measurement conditions and computation conditions depending on whether a blood vessel is an artery or a vein.

It is a second object of the present invention to provide an ophthalmological measurement apparatus that resolves the problem discussed in paragraph (b) above and measures a fundus bloodstream velocity, outputs data used to determine the position of a blood vessel, and obtains information for determining a maximum frequency shift.

These and other objects will be readily apparent to those skilled in the art from a study of the following description of exemplary preferred embodiments.

BRIEF DESCRIPTION OF THE DRAWINGS

FIG. 15 shows a measurement screen of the apparatus.

DESCRIPTION OF THE PREFERRED EMBODIMENTS

Figure 1:
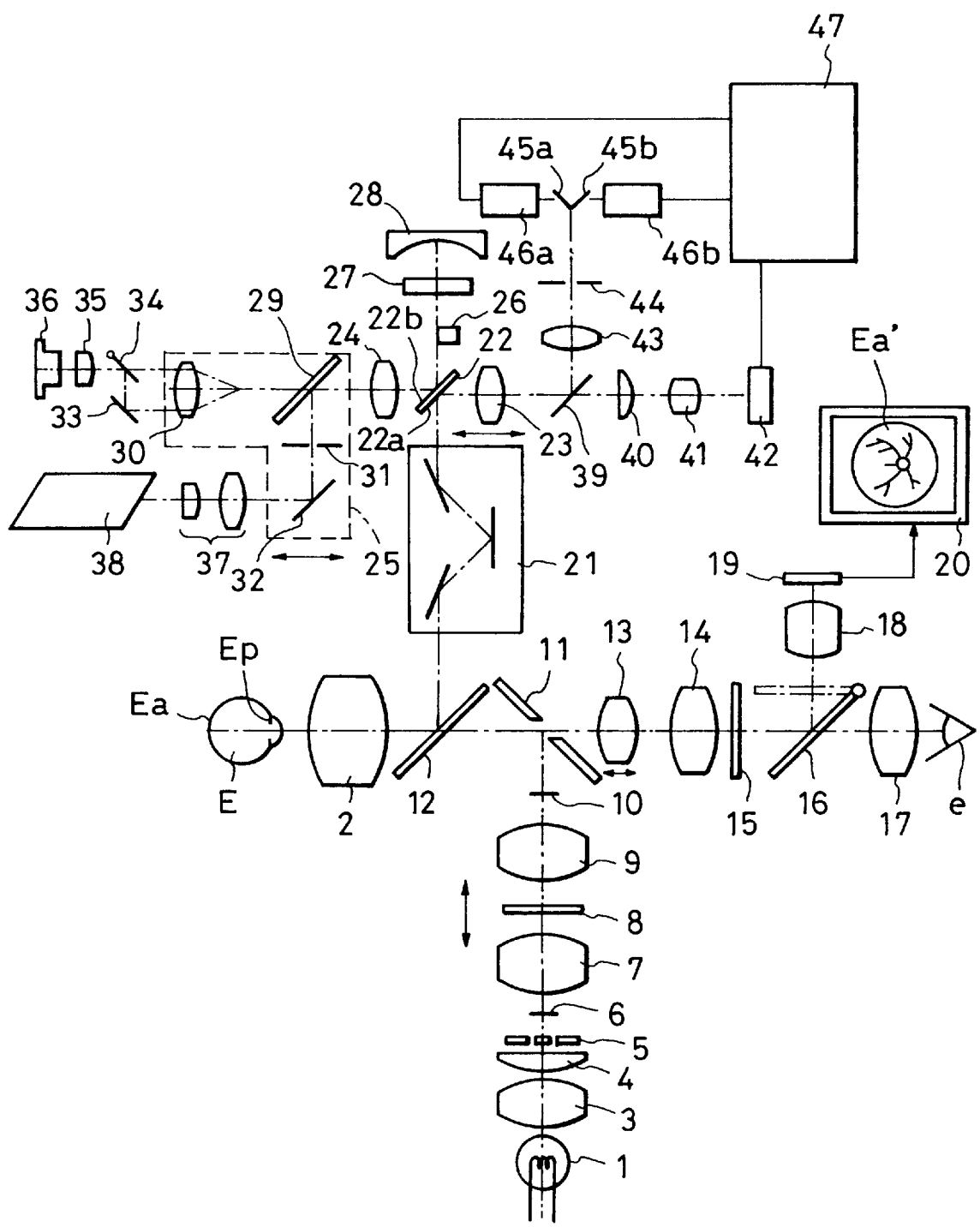
FIG. 1 is a block diagram of a first embodiment of the ophthalmological measurement apparatus of the present invention.

Referring now to the drawings, the embodiments of the present invention are now discussed.

FIG. 1 shows a first embodiment of the fundus bloodstream flowmeter in which the present invention is incorporated. The rheometer includes an illumination optical system in an illumination light path that runs from an observation light source 1 of a tungsten lamp or the like emitting a white light to an objective lens 2 facing an eye E to be measured. The illumination optical system comprises a condenser lens 3, a field lens 4 with a bandpass filter that transmits light beams, for example, in a yellow color region only, a ring slit 5 approximately conjugate with a pupil Ep of the eye to be measured, a light shade member 6 approximately conjugate with the lens of the eye E to be measured, a relay lens 7, a transmission-type liquid-crystal panel 8 as a element for displaying a fixation target, movable along the optical path, a relay lens 9, a light shade member 10 conjugate with the vicinity of the cornea of the eye E to be measured, an apertured mirror 11, and a bandpass mirror 12 for transmitting the light beams in the yellow color region but reflecting most of the remaining light beams in that order along the optical path.

A fundus observation optical system is arranged behind the apertured mirror 11, and comprises a focusing lens 13 movable along the optical path, a relay lens 14, a scale plate 15, an optical path switching mirror 16 retractably arranged in the optical path, and an eyepiece 17 in that order in the optical path to the eye e of an examiner. When the optical path switching mirror 16 is placed in the optical path, a television relay lens 18 and a CCD camera 19 are introduced in the reflection optical path of the optical path switching mirror 16, and the output of the CCD camera 19 is fed to an liquid-crystal monitor display 20.

Disposed in the reflection optical path of the bandpass mirror 12 are an image rotator 21 and a galvanometric mirror 22 with its axis of rotation perpendicular to the page of FIG. 1 and having both surfaces polished. A focusing lens 23 movable along the optical path is arranged in the reflection direction of the lower reflection surface 22a of the galvanometric mirror 22, and a lens 24 and a focusing unit 25 movable along the optical path is arranged on the reflection direction of the upper reflection surface 22b of the galvanometric mirror 22. The front focal plane of the lens 24 is conjugate with the pupil Ep of the eye E to be measured, and the galvanometric mirror 22 is positioned at the front focal plane of the lens 24.

A relay optical system is disposed above the galvanometric mirror 22, and comprises an optical path length compensation semicircle plate 26, a black-point plate 27 presenting a light shading portion in the optical path, and a concave mirror 28 in that order. The relay optical system guides, to the upper reflection surface 22b of the galvanometric mirror 22, a light beam that has passed the galvanometric mirror 22 without being reflected by the lower reflection surface 22a. The optical path length compensation semicircle plate 26 compensates for a vertical offset in FIG. 1, attributed to the difference in position between the upper reflection surface 22b and the lower reflection surface 22a, namely the thickness of the galvanometric mirror 22, and is effective only in the optical path to the image rotator 21.

The focusing unit 25 comprises, in the optical path of the lens 24, a dichroic mirror 29 and a condenser lens 30. The focusing unit 25 also comprises a mask 31 and a mirror 32 in the reflection optical path of the dichroic mirror 29, and is allowed to integrally move in the direction shown by the arrow.

A fixed mirror 33 and an optical path switching mirror 34 retractable from the optical path are disposed, in parallel, in the incident optical path of the lens 30. Disposed in the incident optical path of the optical path switching mirror 34 are a collimator lens 35 and a measurement light source 36, such as a laser diode, for emitting a coherent light, such as a red color light. Disposed in the incident optical path of the mirror 32 are a beam expander 37 including a cylindrical lens and the like, and a tracking light source 38, such as an He—Ne laser light source for emitting a green color light, different from other light sources in that it is highly bright.

A blood vessel detection optical system is arranged in the reflection optical path from the lower reflection surface 22a of the galvanometric mirror 22, and comprises the focusing lens 23, a dichroic mirror 39, a field lens 40, a magnifying lens 41, and a one-dimensional CCD 42 with an image intensifier in that order in the optical path. A measurement light receiving optical system is disposed in the reflection optical path of the dichroic mirror 39 and comprises an imaging lens 43, a confocal diaphragm 44, a pair of mirrors 45a, 45b approximately conjugate with the pupil Ep of the eye E to be measured, and further photomultipliers 46a, 46b to the reflection directions of the respective mirrors 45a, 45b. Although all optical paths, for convenience of drawing, are shown on the same plane, the reflection optical paths of the mirrors 45a, 45b, the measurement optical path in the reflection direction of the tracking light source 38, and the optical path from the measuring light source to the mask 31 are respectively perpendicular to the page of FIG. 1. The outputs of the one-dimensional CCD 42, and photomultipliers 46a, 46b are fed to a control block 47.

Figure 2:
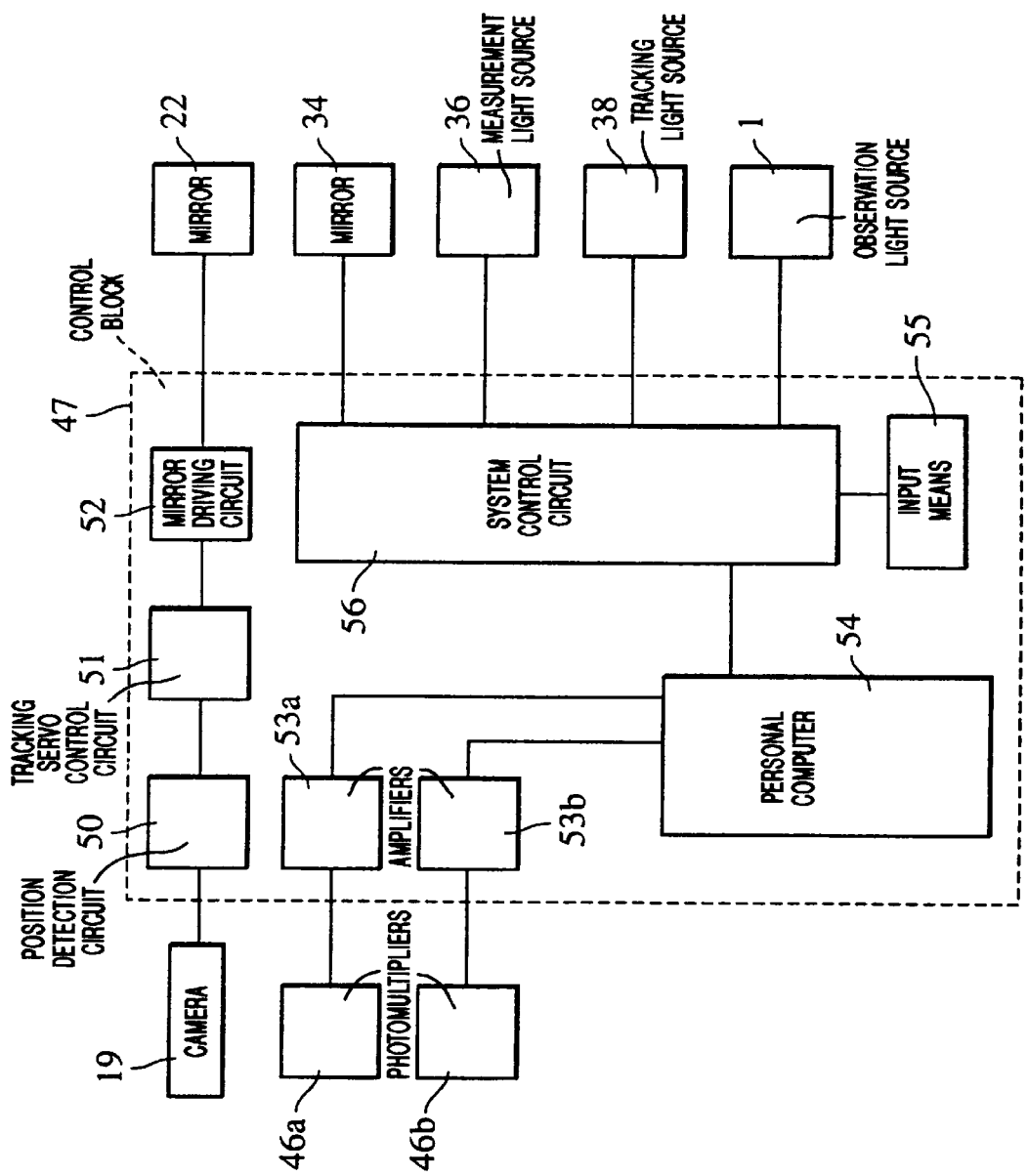
FIG. 2 is a block diagram of the control block of the ophthalmological measurement apparatus.

FIG. 2 is a block diagram of the control block 47. The output of the CCD camera 19 is fed through a blood vessel position detection circuit 50, a tracking servo control circuit 51 and a galvanometric mirror driving circuit 52 to the external galvanometric mirror 22. The outputs of the photomultipliers 46a, 46b are connected via amplifiers 53a, 53b, respectively, to a personal computer 54. The outputs of the personal computer 54 and input means 55 are fed to a system control circuit 56. The outputs of the system control circuit 56 are respectively fed to the observation light source 1, optical path switching mirror 34, measurement light source 36, and tracking light source 38.

Figure 3:
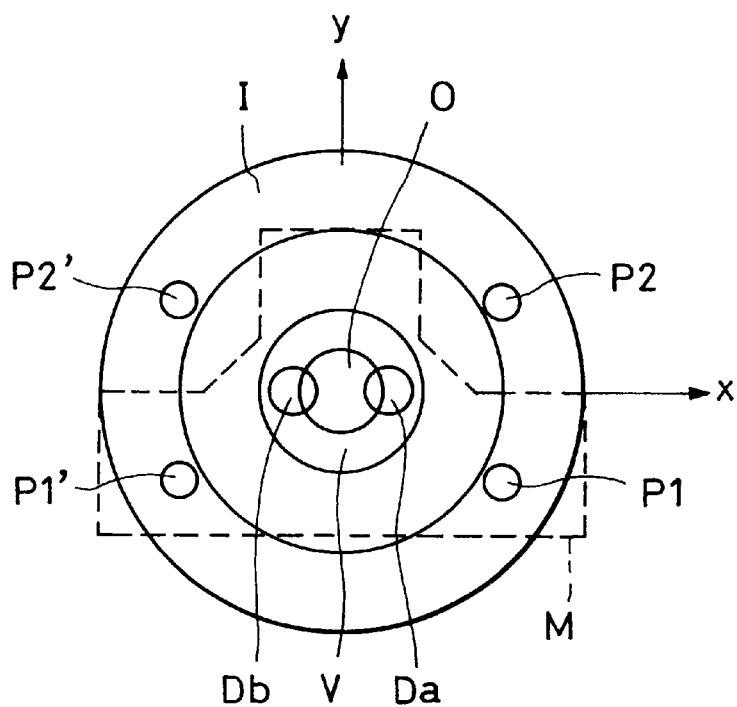
FIG. 3 is an explanatory view of the layout of light beams on a pupil.

FIG. 3 shows the layout of light beams on the pupil Ep of the eye E to be measured. Shown in FIG. 3 are an image I of the ring slit 5 that is an area illuminated by the yellow illumination light, an image O of an aperture of the apertured mirror 11, which is caused by a fundus observation light beam, an image V of the effective section of the upper and lower reflection surfaces 22a, 22b of the galvanometric mirror 22 caused by measurement/blood vessel received light beams, and images Da, Db of the pair of mirrors 45a, 45b, caused by two measurement received light beams. P2 and P2' represent positions of incidence of measurement light beams, and are selected by controlling the optical path switching mirror 34. An area M enclosed by a broken line is the image of the lower reflection surface 22a of the galvanometric mirror 22.

The white light beam emitted from the observation light source 1 passes through the condenser lens 3 and reaches the field lens 4, which transmits only the yellow wavelength light therethrough. The yellow wavelength light then passes the ring slit 5, light shade member 6, and relay lens 7, and illuminates the transmission-type liquid-crystal panel 8 from behind. The yellow wavelength light beam further passes the relay lens 9 and light shade member 10, and is reflected by the apertured mirror 11. The yellow wavelength light beam only passes the bandpass mirror 12 and objective lens 2 as the fundus illumination light beam, is once focused as the image I on the pupil Ep of the eye E to be measured, and then uniformly illuminates the fundus Ea.

The transmission-type liquid-crystal panel 8 presents a fixation target, which is projected as a fixation image on the fundus Ea of the eye E by the illumination light. The ring slit 5, and light shade members 6 and 10 are used to separate the fundus illumination light from the fundus observation light on the front portion of the eye E. Their forms are not important as long as they offer a required light shade area.

The light reflected from the fundus Ea is returned through the pupil Ep as the reflected fundus observation light beam O and follows the same optical path to the apertured mirror 11. The fundus observation light beam O then passes the opening in the center of the apertured mirror 11, focusing lens 13 and relay lens 14, and is then focused as the fundus image Ea on the scale plate 15, and reaches the optical path switching mirror 16. When the optical path switching mirror 16 is retracted from the optical path, the examiner's eye e can observe a fundus image Ea' through the eyepiece 17. When the optical path switching mirror 16 is positioned in the optical path, the image Ea' focused on the scale plate 15 is re-focused through the television relay lens 18 on the CCD camera 19 and is then presented on the liquid-crystal monitor display 20.

The examiner performs the aligning of the apparatus observing the fundus image Ea' through the eyepiece 17 or the liquid-crystal monitor display 20. Both may be selectively used depending on the purpose of the examination. Since the eyepiece 17 typically permits a higher discrimination and a higher sensitivity in observation than the liquid-crystal monitor display 20, the use of the eyepiece 17 is suited to a diagnosis that involves detecting a slight change in the fundus Ea. In the observation with the liquid-crystal monitor display 20, however, the examiner's fatigue is lessened because it is not necessary to concentrate his or her field of view. Furthermore, the output of the CCD camera 19 may be output to a video cassette recorder or a video printer to sequentially electronically record the region of measurement in the fundus Ea. Such recording is clinically quite useful.

The measurement light emitted from the measurement light source 36 is collimated through the collimator lens 35, is reflected by the optical path switching mirror 34 and then by the fixed mirror 33 when the optical path switching mirror 34 is placed in the optical path, and passes through the lower portion of the condenser lens 30. When the optical path switching mirror 34 is retracted from the optical path, the measurement light passes through the upper portion of the condenser lens 30. In both cases, the measurement light is transmitted through the dichroic mirror 29.

The beam expander 37 expands the tracking light, emitted from the tracking light source 38, in its beam width at different ratios from the horizontal direction to the vertical direction transversely across the beam. The expanded beam is reflected by the mirror 32 and is directed to the shaping mask 31 where the beam is shaped to a desired shape. The beam is then reflected by the dichroic mirror 29, and is superimposed on the spot measurement light beam focused by the condenser lens 30 at a position which is conjugate with the center of the opening of the mask 31.

The superimposed measurement light and tracking light pass through the lens 24, are reflected by the upper surface 22b of the galvanometric mirror 22, pass the black-point plate 27, are reflected by the concave mirror 28, passes again the black-point plate 27 and then the optical path length compensation semicircle plate 26, and are returned to the galvanometric mirror 22. The galvanometric mirror 22 is mounted at a position conjugate with the pupil Ep of the eye E to be measured, and the shape of the galvanometric mirror 22 on the pupil Ep of the eye E to be measured is as shown by the area M enclosed by the broken line in FIG. 3.

The concave mirror 28, the black-point plate 27 and the optical path length compensation semicircle plate 26 are co-linearly arranged in the optical path, and constitute the relay optical system that has a function of imaging the upper reflection surface 22b and the lower reflection surface 22a of the galvanometric mirror 22 at a magnification of −1. By placing or retracting the optical path switching mirror 34 into or from the optical path, the light beams reflected from positions P1, P1' in FIG. 3, on the back of the image M of the galvanometric mirror 22, are returned to positions P2, P2' on the cutout portions of the galvanometric mirror 22, and are thus directed to the image rotator 21 without being reflected by the galvanometric mirror 22. The light beams passing through the image rotator 21 are deflected by the bandpass mirror 12 toward the objective lens 2, and illuminate the fundus Ea of the eye E via the objective lens 2.

In this way, the measurement light beam and the tracking light beam are reflected by the upper reflection surface 22b of the galvanometric mirror 22. When returned to the galvanometric mirror 22, the measurement light beam and the tracking light beam are offset from the optical path of the objective lens 2. The beams are thus focused on the pupil Ep as the spot images P2 and P2' as shown in FIG. 3 and then illuminate the fundus Ea in spots.

A light reflected and scattered by the fundus Ea is converged by the objective lens 2, is reflected by the bandpass mirror 12, passes through the image rotator 21, is reflected by the lower reflection surface 22a of the galvanometric mirror 22, passes through the focusing lens 23, and is separated by the dichroic mirror 39 into a measurement light beam and a tracking light beam.

The tracking light is transmitted through the dichroic mirror 39, and is focused on the one-dimensional CCD 42 via the field lens 40 and magnifying lens 41 as an enlarged blood vessel image Ev' that is more magnified than the fundus image Ea' by the fundus observation optical system. Based on the blood vessel image Ev' imaged by the one-dimensional CCD 42, the blood vessel position detection circuit 50 produces data indicative of the offset quantity of the blood vessel image Ev' from the center of tracking. The data is fed to the galvanometric mirror 22 via the tracking servo control circuit 51 and the galvanometric mirror driving circuit 52 so that the blood vessel image Ev' is aligned with the center of tracking with no offset.

On the other hand, the measurement light is reflected by the dichroic mirror 39, passes through the imaging lens 43 and the opening of the confocal diaphragm 44, and is reflected by the pair of mirrors 45a, 45b, and the reflected beams are respectively received by the photomultipliers 46a, 46b. The outputs of the photomultipliers 46a, 46b are respectively amplified by the amplifiers 53a, 53b and fed to unshown A/D converters in the personal computer 54. Digital signals from the A/D converters are stored in a memory in the personal computer 54, and frequency-analyzed to determine the bloodstream velocity in the fundus Ea in the same manner as the conventional art. The system control circuit 56 controls the observation light source 1, the measurement light source 36, and the tracking light source 38 to light or extinguish them, and controls the optical path switching mirror 34 to place or retract it, to or from, the optical path.

Figure 4:
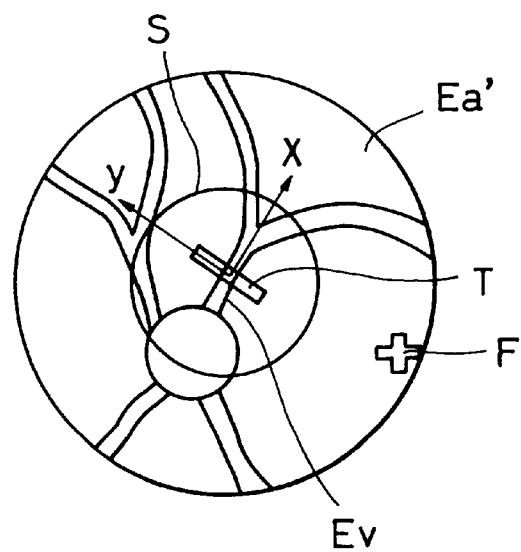
FIG. 4 is an explanatory view of an observed fundus image.

Part of the light reflected and scattered from the fundus Ea, in response to the measurement light beam and the tracking light beam, is transmitted through the bandpass mirror 12, and is guided to the fundus observation optical system behind the apertured mirror 11. The tracking light is focused as a bar-shaped indicator T on the scale plate 15, while the measurement light is focused as a spot image on the center of the indicator T. These images are observed along with the fundus image Ea' and a fixation target image F through the eyepiece 17 or the liquid-crystal monitor display 20 as shown in FIG. 4. An unshown spot image superimposed on the center of the indicator T is also observed. By manipulating an operational member, such as an operation lever of the input means 55, the indicator T is one-dimensionally moved within a regular circle S centered on the center of the field of view and provided on the scale plate 15 that is projected on the fundus Ea.

The examiner first focuses the fundus image Ea' shown in FIG. 4. As an unshown focus knob in the input means 55 is adjusted, unshown driving means moves the transmission-type liquid-crystal panel 8, focusing lenses 13, 23, and focusing unit 25 in integral motion along the optical path. When the fundus image Ea' is focused, the transmission-type liquid-crystal panel 8, the scale plate 15, the one-dimensional CCD 42 and the confocal diaphragm 44 become concurrently conjugate with the fundus Ea.

When the focusing is complete, the examiner operates the input means 55 to move the fixation target image F, guides the subject's eyes in a direction to change the region of measurement, and shifts a blood vessel Ev to be measured into the circle S of the scale plate 15. Manipulating the unshown operational lever of the input means 55, the image rotator 21 is operated to rotate the indicator T so that the indicator T is perpendicular to the direction of extension of the blood vessel Ev to be measured.

Since the fundus observation light comes in not via the image rotator 21, it will be understood that the indicator T only rotates. The images of the optical components shown in FIG. 2 on the pupil Ep are rotated about the origin by the same angle of rotation. A line connecting the centers of the measurement received light beams Da, Db and a line connecting the centers of the spot images P1, P1', or P2, P2', namely, the x axis, agree with the direction of the extension of the blood vessel Ev.

When the alignment of the blood vessel is complete, the indicator T is shifted in the direction of the arrow by manipulating the operational lever of the input means 55 until the blood vessel comes to the center of the indicator T.

After selecting the region of measurement, the examiner inputs, through the unshown input means of the personal computer 54, a signal indicating whether the region of measurement is in an artery or a vein. The personal computer 54 communicates with the system control circuit 56, for example, to set the data acquisition time for measurement to 2 seconds for an artery and 0.5 second for a vein, the quantity of data for frequency analysis to 512 pieces of data for the artery and 1024 pieces of data for the vein. By manipulating the input means 55, the initiation command of a tracking operation is input.

Figure 5:
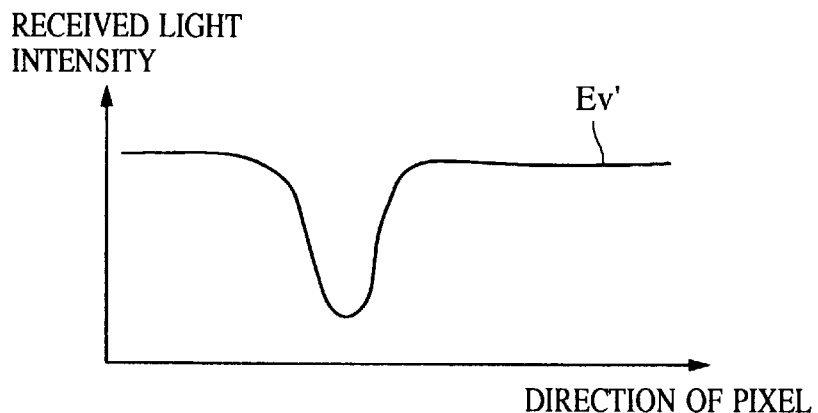
FIG. 5 is a waveform diagram of a one-dimensional CCD of the ophthalmological measurement apparatus.

When the tracking initiation command is input to the system control circuit 56 from the input means 55, the blood vessel position detection circuit 50 calculates the offset of the blood vessel image Ev' from a one-dimensional reference position, based on the received signal of the one-dimensional CCD 42. In response to the offset value, the tracking servo control circuit 51 and galvanometric mirror driving circuit 52 drive the galvanometric mirror 22 until the position of the blood vessel image Ev' is fixed on the one-dimensional CCD 42. FIG. 5 is a graph showing the received light intensity of the blood vessel image Ev'. The ordinate represents the received light intensity of the one-dimensional CCD 42, while the abscissa represents the direction of the pixel array of the one-dimensional CCD 42. The received light intensity drops at the blood vessel Ev.

After confirming the initiation of the tracking operation, the examiner presses an unshown measurement switch in the input means 55 to start a measurement. The system control circuit 56 places the optical path switching mirror 34 in the optical path. The light beams incident on the spot images P1, P2 on the pupil Ep of the eye E to be measured are first received by the photomultipliers 46a, 46b, and A/D converted by the A/D converters, and acquired by the personal computer 54 during the data acquisition time that is predetermined depending on whether the region of measurement is in the artery or the vein.

In response to the signal from the system control circuit 56, the optical path switching mirror 34 is retracted from the optical path, the light beams entering at the positions of the spot images P1', P2' on the pupil Ep of the eye E to be measured are received by the photomultipliers 46a, 46b, respectively, A/D converted by the A/D converters, and acquired by the personal computer 54 during the data acquisition time that is predetermined depending on whether the region of measurement is in the artery or the vein. These data are subjected to frequency analysis computation in the personal computer 54 to determine a doppler shift frequency. The frequency analysis computation is carried out by subjecting, to an FFT process, time-series data, the quantity of which is dependent on whether the artery or the vein is measured.

Since the artery changes its bloodstream velocity periodically in synchronism with the heartbeat cycle of contraction and expansion, it needs to be measured for at least one cycle. On the other hand, a short-time measurement is sufficient in the vein, because no such periodic change takes place in the bloodstream. Since the bloodstream velocity in the artery sharply increases at each contraction phase of the heart, the quantity of data of the artery to be used in the FFT process is set to be smaller than that of the vein.

Figure 6A:
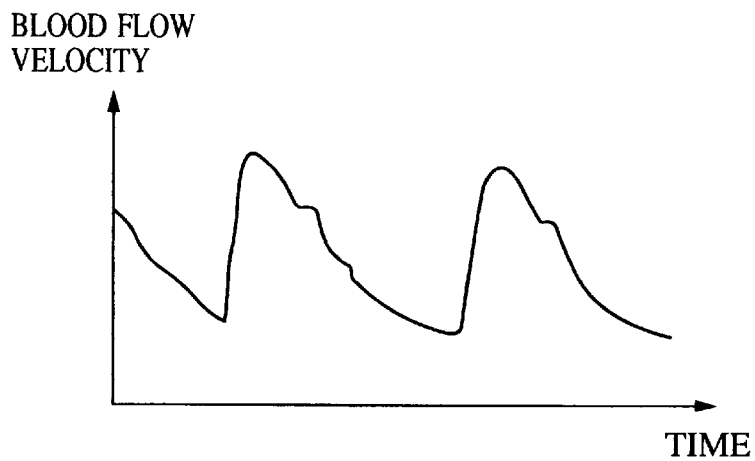
FIGS. 6A and 6B are waveform diagrams of bloodstream velocities.
Figure 6B:
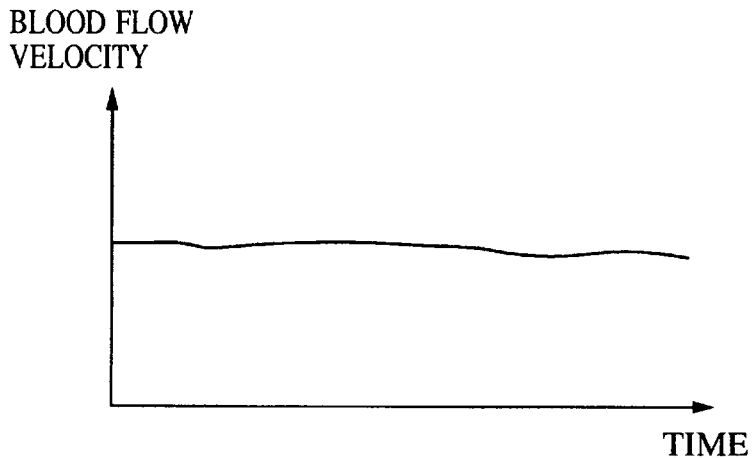

In this embodiment, the sampling time of the received signal of the photomultipliers 46a, 46b is set to be 10 μs. In the artery measurement, 512 pieces of data are used in one FFT process, and the bloodstream velocity data is computed every about 5 ms. Even if the bloodstream velocity changes, its waveform is accurately reproduced. In the vein measurement, 1024 pieces of data are used in one FFT process, and bloodstream velocity data is computed every about 10 ms. As a result, data available for the vein measurement is half the data quantity available for the artery measurement. This presents no problem, because the vein has no substantial velocity change. Measurement accuracy in the vein is increased, because the frequency resolution in the frequency analysis process is twice that of the artery. FIG. 6A illustrates one example of the artery bloodstream velocity, wherein the ordinate represents the bloodstream velocity while the abscissa represents time. FIG. 6B illustrates one example of the vein bloodstream velocity.

The light beams entering the positions of the spot images P1, P2 on the pupil Ep of the eye E to be measured are received by the photomultipliers 46a, 46b, the doppler shift frequencies Δfmax1, Δfmax2 are derived from these received signals, and the maximum bloodstream velocity Vmax is obtained. The light beams entering at the positions of the spot images P1', P2' are also received by the photomultipliers 46a, 46b, the doppler shift frequencies Δfmax1', Δfmax2' are derived from these received signals, and the maximum bloodstream velocity Vmax' is obtained.

When one position of incidence only is used, the sign of the doppler shift has to be inverted to calculate the maximum bloodstream velocity Vmax depending on the angle of incident on the blood vessel Ev. When two positions of incidence are used in measurement as described above, a true bloodstream velocity is easily obtained by comparing the two maximum bloodstream velocities Vmax, Vmax'.

When both maximum bloodstream velocities Vmax, Vmax' need no sign inversion, both Vmax and Vmax', approximately equal to each other, represent a true bloodstream velocity. When one is greater in value than the other, the greater one is the true bloodstream velocity. In this case, however, the smaller one may be re-computed with its sign inverted to derive the true bloodstream velocity. As a result, all data measured contribute to the determination of the true bloodstream velocity.

In this embodiment, the determination process is performed by acquiring the signals at two positions of incidence for a predetermined period of time. Alternatively, a short-time preliminary measurement may be performed to determine which one needs a sign determination process, and data may be acquired at one position of incidence only.

Figure 7:
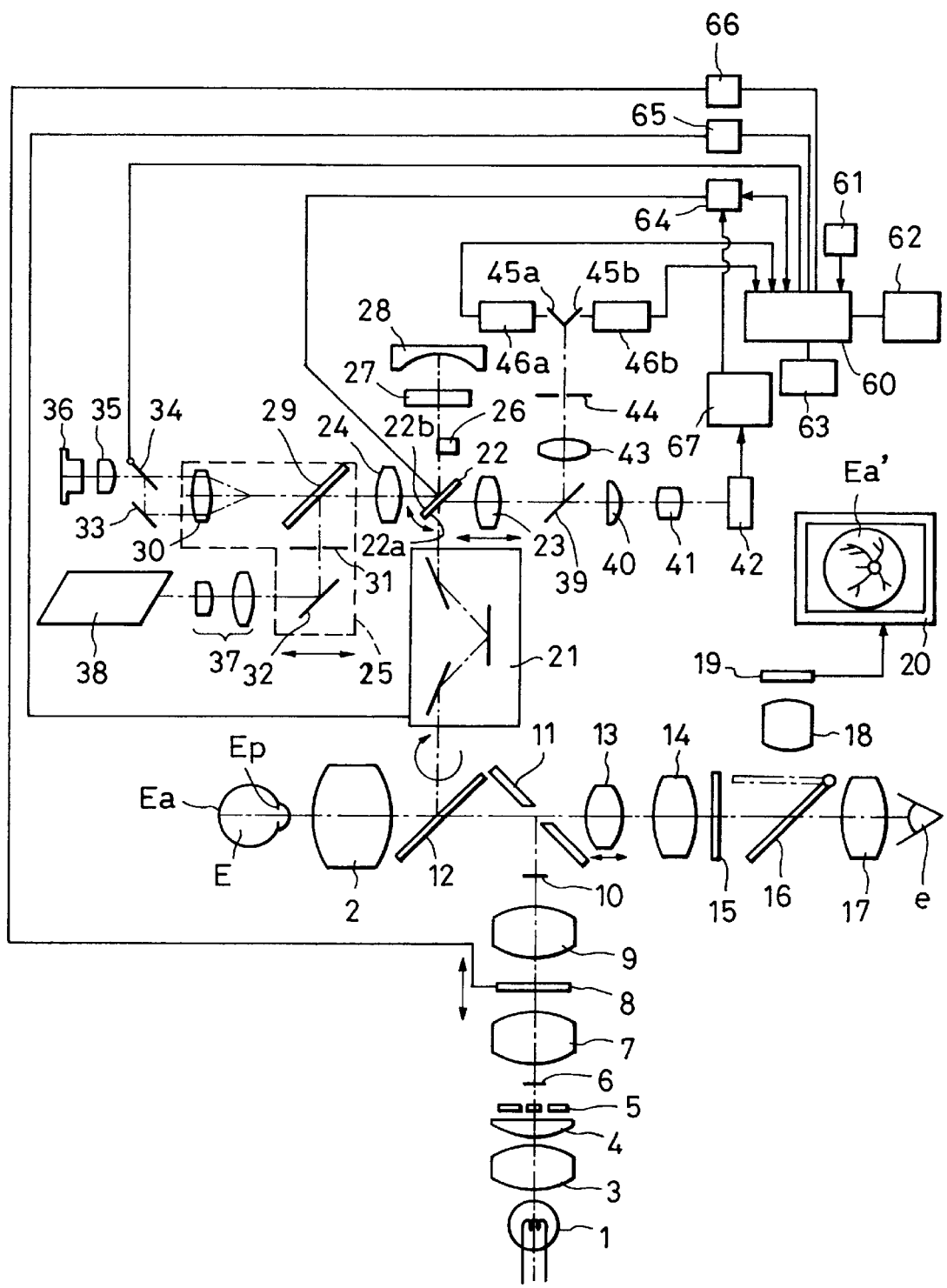
FIG. 7 is a block diagram of a second embodiment of the ophthalmological measurement apparatus of the present invention.

FIG. 7 shows a second embodiment of the present invention. Most of the optical system in the second embodiment is common to that of the first embodiment. The control system corresponding to the control block 47 in the first embodiment is a system control circuit 60 for controlling generally the apparatus. The system control circuit 60 is connected to input means 61 manipulated by the examiner, display means 62 for presenting measurement results, and memory means 63 for storing a diversity of data. The system control circuit 60 receives the outputs of the photomultipliers 46a, 46b. The outputs of the system control circuit 60 are respectively fed to a driving circuit 64 for controlling the galvanometric mirror 22, a control circuit 65 for controlling the image rotator 21, a control circuit 66 for controlling the transmission-type liquid-crystal panel 8, and the optical path switching mirror 34. The output of the one-dimensional CCD 42 is connected to the driving circuit 64 via a blood vessel position detection circuit 67.

Figure 8:
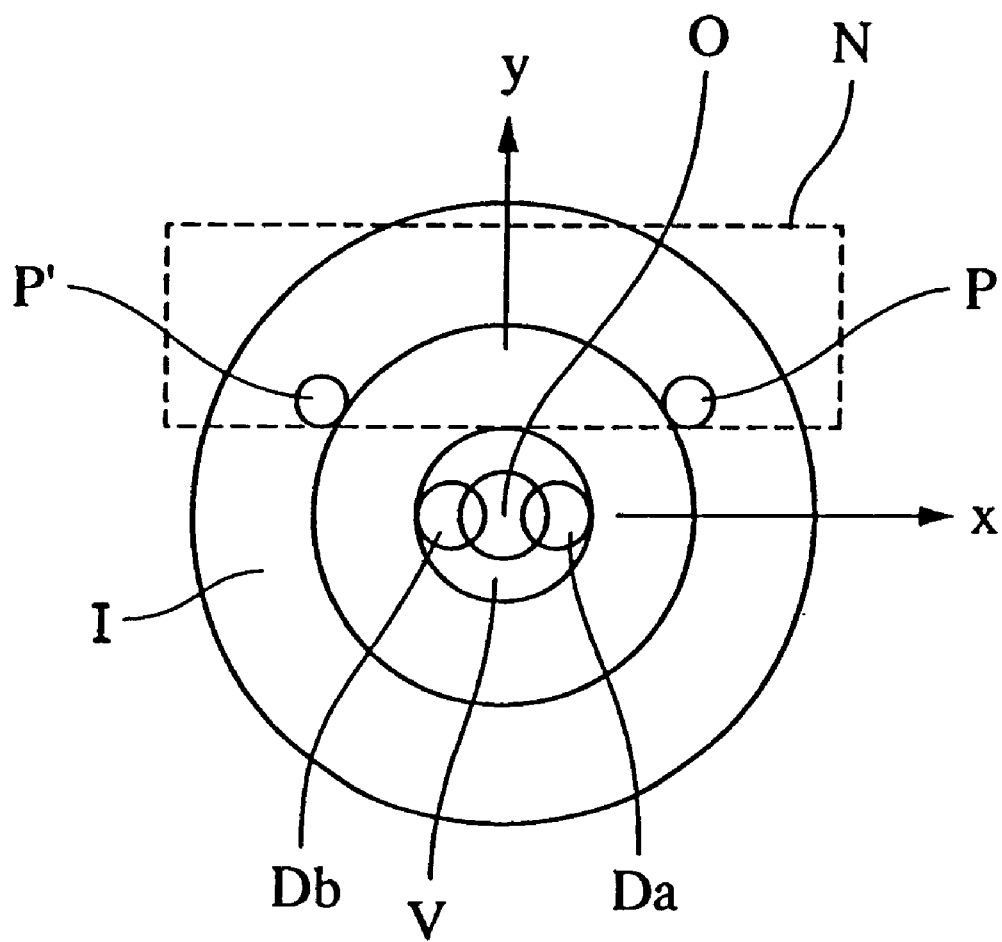
FIG. 8 is an explanatory view of the layout of light beams on a pupil.

FIG. 8 shows the layout of light beams on the pupil Ep of the eye E to be measured. Shown in FIG. 8 are an image I of the ring slit 5 that is an area illuminated by the yellow illumination light, an image O of an aperture of the apertured mirror 11 which is caused by a fundus observation light beam, an image V of the effective section of the upper and lower reflection surfaces of the galvanometric mirror 22 caused by measurement/blood vessel received light beams, and images Da, Db of the pair of mirrors 45a, 45b, caused by two measurement received light beams. P and P' represent positions of incidence of measurement light beams, and are selected by controlling the optical path switching mirror 34. An area N enclosed by a broken line is the image of the lower reflection surface 22a of the galvanometric mirror 22.

The illumination optical system, the fundus observation optical system, the blood vessel detection optical system and the measurement light receiving optical system are almost the same as those in the first embodiment, and their description will not be repeated.

The tracking light beam emitted from the tracking light source 38 is transmitted through the dichroic mirror 39, and is focused on the one-dimensional CCD 42 via the field lens 40 and magnifying lens 41 as an enlarged blood vessel image Ev' that is more magnified than the fundus image Ea' by the fundus observation optical system. Based on the blood vessel image Ev' imaged by the one-dimensional CCD 42, the blood vessel position detection circuit 67 produces data indicative of the offset quantity of the blood vessel image Ev' from the center of tracking. The data is fed the driving circuit 64, which drives the galvanometric mirror 22 to correct the offset.

Figure 9:
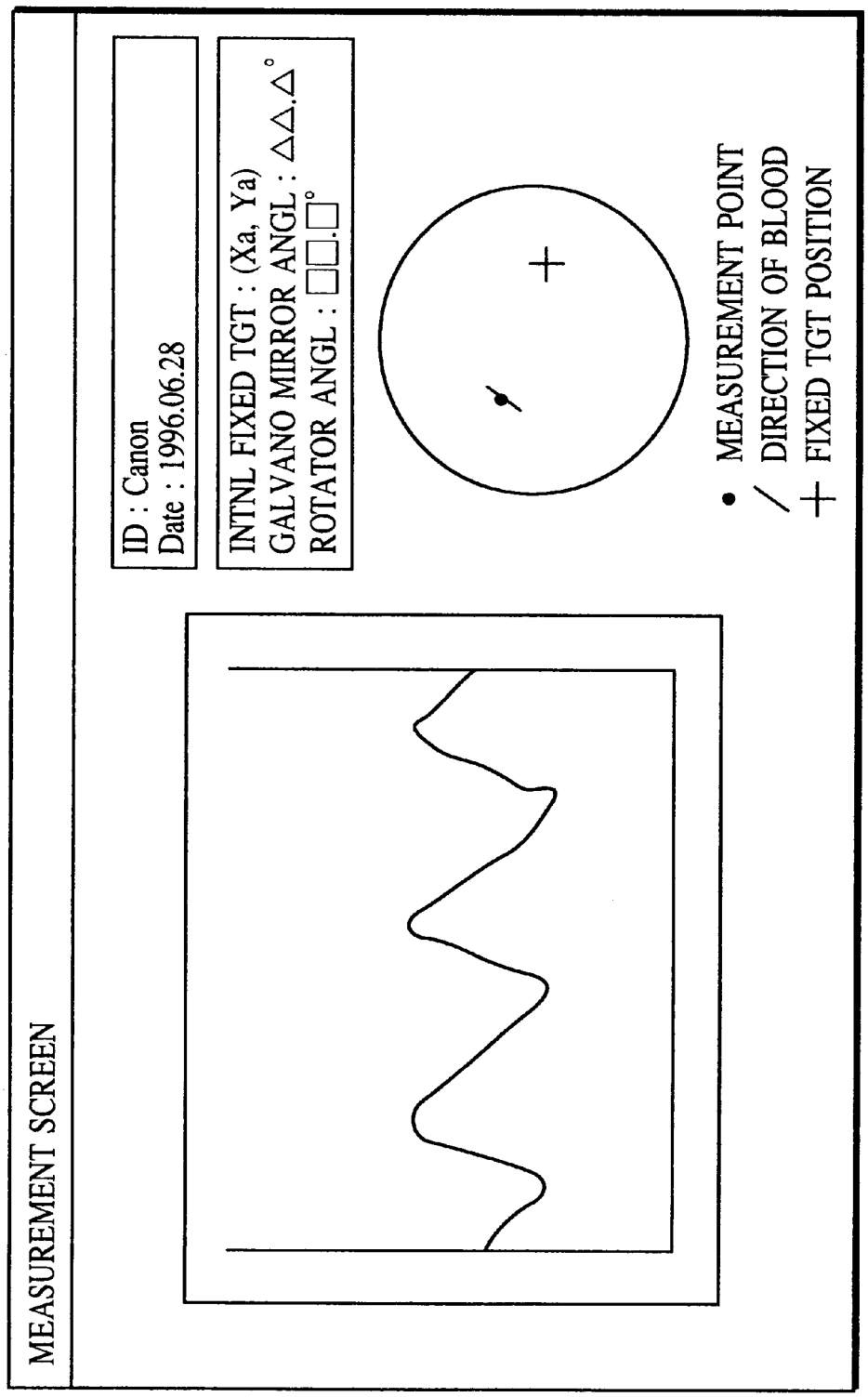
FIG. 9 shows a measurement screen of the apparatus.

On the other hand, the measurement light from the measurement light source 36 is reflected by the dichroic mirror 39, passes through the imaging lens 43 and the opening of the confocal diaphragm 44, and is reflected by the pair of mirrors 45a, 45b, and the reflected beams are respectively received by the photomultipliers 46a, 46b. The outputs of the photomultipliers 46a, 46b are respectively fed to the system control circuit 60, where the received light signals are frequency analyzed to determine the bloodstream velocity at the fundus Ea. The measurement results are presented on the display means 62. As shown in FIG. 9 in this embodiment, the angle of the image rotator 21, the angle of the galvanometric mirror 22, and the position information of the fixation target F of the transmission-type liquid-crystal panel 8 along with the measurement results of the bloodstream velocity, during measurement, are not only stored in the memory means 63 but also presented on the display means 62. With this arrangement, the examiner easily identifies the point of the blood vessel Ev where the actual measured value of bloodstream velocity is detected.

Part of the light reflected and scattered from the fundus Ea in response to the measurement light beam and the tracking light beam is transmitted through the bandpass mirror 12, and is guided to the fundus observation optical system behind the apertured mirror 11. The tracking light is focused as a bar-shaped indicator T on the scale plate 15, while the measurement light is focused as a spot image on the center of the indicator T.

Figure 10:
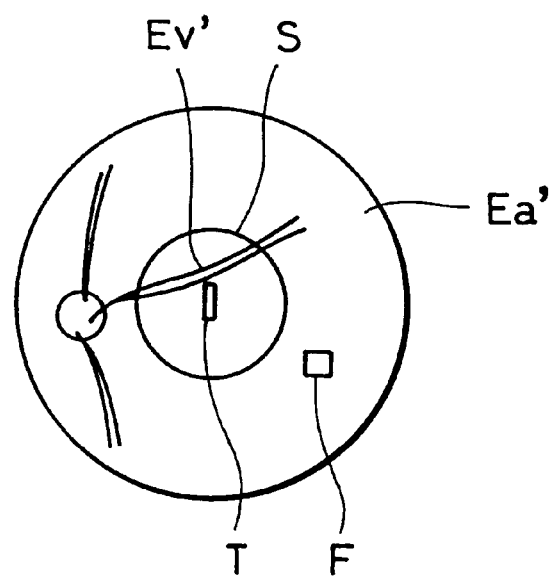
FIG. 10 shows an observed fundus image.

FIG. 10 shows the fundus image Ea'. The fixation target image F along with the fundus image Ea' is observed through the eyepiece 17 or the liquid-crystal monitor display 20. An unshown spot image superimposed on the center of the indicator T is also observed. By manipulating an operational, member such as an operation lever of the input means 61, the indicator T is one-dimensionally moved within a regular circle S centered on the center of the field of view and provided on the scale plate 15 that is projected on the fundus Ea.

The examiner first focuses the fundus image Ea'. As an unshown focus knob in the input means 61 is adjusted, unshown driving means moves the transmission-type liquid-crystal panel 8, focusing lenses 13, 23, and focusing unit 25 in integral motion along the optical path. When the fundus image Ea' is focused, the transmission-type liquid-crystal panel 8, the scale plate 15, the one-dimensional CCD 42 and the confocal diaphragm 44 become concurrently conjugate with the fundus Ea. In actual measurements, the examiner sets the depth of the blood vessel to be measured and focuses the fundus image Ea' observing the fundus image Ea' as shown in FIG. 10.

Figure 11:
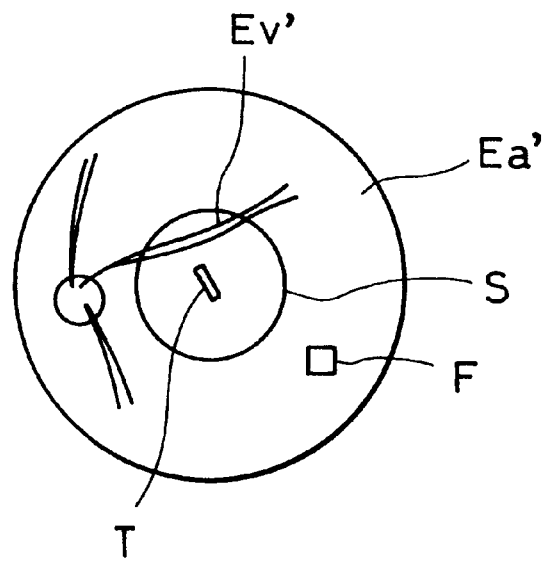
FIG. 11 shows an observed fundus image.
Figure 12:
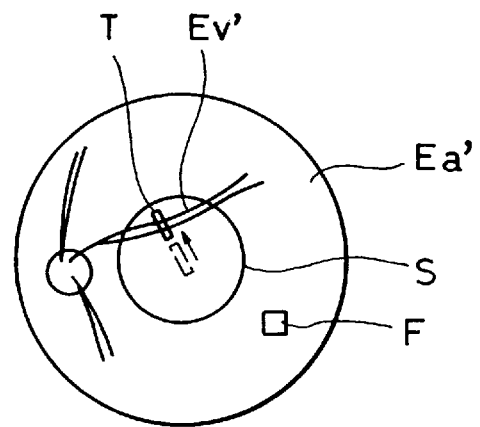
FIG. 12 shows an observed fundus image.

When the focusing is complete, the examiner operates the input means 61 which causes the system control circuit 60 to drive the control circuit 66 for controlling the transmission-type liquid-crystal panel 8. The examiner thus moves the fixation target image F on the transmission-type liquid-crystal panel 8, guides the subject's eyes E in a direction to change the region of measurement, and shifts a blood vessel Ev to be measured into the circle S of the scale plate 15. The examiner then manipulates the operational lever of the input means 61. In response, the system control circuit 60 drives the control circuit 65 to rotate the image rotator 21. As shown in FIGS. 11 and 12, the indicator is rotated such that the indicator T is perpendicular to the direction of the extension of the blood vessel Ev to be measured.

After confirming the initiation of the tracking operation, the examiner presses an unshown measurement switch in the input means 61 to start a measurement. The system control circuit 60 stores, in its memory means 63, the angle information of the image rotator 21, the angle information of the galvanometric mirror 22, and the position information of the fixation target image F. The system control circuit 60 then places the optical path switching mirror 34 in the optical path. The light beam entering at the position of the spot image P on the pupil Ep of the eye E to be measured is first received by the photomultipliers 46a, 46b, and the received light signals are acquired by the system control circuit 60. The maximum frequency shifts |Δfmax1|, |Δfmax2| are determined there. The maximum frequency shifts |Δfmax1|, |Δfmax2| are the results obtained by frequency analyzing the output signals from the photomultipliers 46a, 46b.

The light beam is positioned at the spot image P, and is sufficiently displaced from the measurement received light beams Da, Db. The maximum bloodstream velocity Vmax is determined by substituting cos β=1 in equation (1), thus determined from Vmax={λ/(n·α)}·||Δfmax1|−|Δfmax2||. Depending on the position of the blood vessel Ev in the fundus Ea, there is a case where the maximum velocity has to be computed from Vmax={λ/(n·α)}·||Δfmax1|+|Δfmax2||. In this embodiment, during the first half stage of measurement, the maximum velocity Vmax is computed from equation (1). During the second half stage of measurement, the system control circuit 60 retracts the optical path switching mirror 34 from the optical path to measure with the light beam entered at the position of the spot image P' on the pupil Ep of the eye E to be measured.

As shown in FIG. 8, the line segment connecting the centers of the spot images P, P' on the pupil Ep is drawn in parallel with the line segment connecting the centers of the measurement received light beams Da, Db. In this embodiment, the separation between the spot images P, P' is set to be greater than the separation between the measurement received light beams Da, Db. The line connecting the centers of both line segments is perpendicular to each line segment.

After the incident light position is switched from the spot image P to the spot image P', the system control circuit 60 receives the signals from the two photomultipliers 46a, 46b, computes the maximum frequency shifts |Δfmax1'|, |Δfmax2'|, and determines the maximum bloodstream velocity Vmax' according to equation (1). Selecting the incident light, as described above, helps differentiate an area of φi shown in FIG. 13, where the signs of maximum frequency shifts |Δfmax1|, |Δfmax2| are inverted, from an area where the signs of the maximum frequency shifts |Δfmax1'|, |Δfmax2'| are inverted. In the area where no sign simultaneous inversions take place, the maximum bloodstream velocities Vmax≈Vmax', while the relationship of (one maximum velocity with no sign inversion taking place)>(the other maximum velocity with a sign inversion taking place) results where sign inversions take place in either of both maximum bloodstream velocities Vmax, Vmax'. The system control circuit 60 selects the proper equation for each of the first and second half stages of the measurement by comparing the maximum bloodstream velocities Vmax, Vmax'. The maximum bloodstream velocities Vmax, Vmax' computed by the system control circuit 60 are presented on the display means 62. Along with the measurement results, the angle information of the image rotator 21, the angle information of the galvanometric mirror 22, and the position information of the fixation target F of the transmission-type liquid-crystal panel 8, all stored in the memory means 63, are presented on the display means 62.

Figure 14:
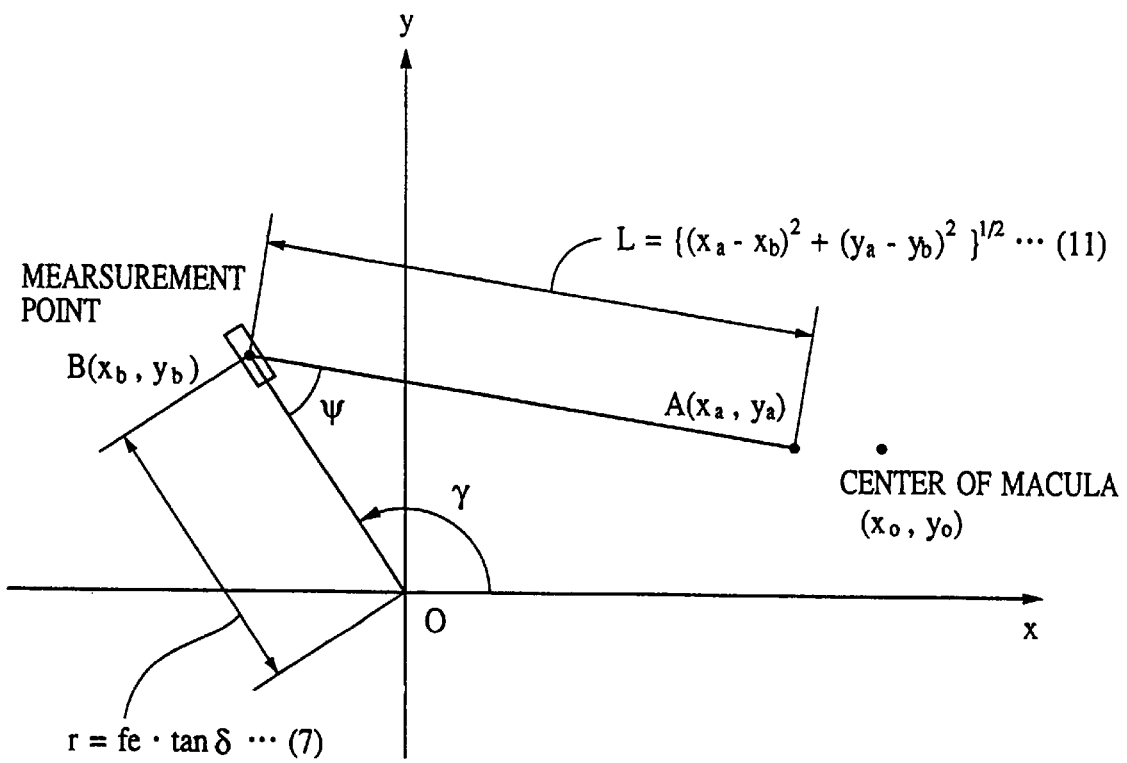
FIG. 14 is an explanatory view showing the relationship between the region of measurement and the centroid of a yellow spot.

FIG. 14 shows the relationship of the region of measurement to the centroid of a yellow spot. If m/m' represent the magnification of the fundus image Ea'/fixation target image F, (X0, Y0) represent the coordinates of the fixation target F on the transmission-type liquid-crystal panel 8, (0, 0) represent the coordinates of the optical axis of the objective lens 2 on the fundus Ea or on the transmission-type liquid-crystal panel 8, and (x0, y0) represent the coordinates of the center of the macula on the fundus Ea, then the following equations hold true:

$$x0 = (m'/m)X0 \qquad (2)$$

$$y0 = (m'/m)Y0 \qquad (3).$$

It is known that the optical axis of symmetry of the eye is deflected by about 5° to the ear side from the visual axis of the eye indicating the line of sight of the eye (the line connecting the center of the macula providing the maximum vision to the nodal point). If a typical value fe of a model eye represents the focal length of the eye E to be measured, and (xa, ya) represents the coordinates of the optical axis of the objective lens 2 on the retina, equations (4) and (5) hold true as follows:

$$xa = (m'/m) \cdot (X0 \pm fe \cdot \tan 5°) \quad (4)$$

$$ya = (m'/m) Y0 \quad (5).$$

The signs ± are determined depending on whether the eye E to be measured is the left one or the right one.

If n/n' represents the magnification of the galvanometric mirror 22/pupil Ep of the eye E to be measured, δ represents the angle of swing of the galvanometric mirror 22, and δ' the angle of incidence of the tracking light beam and measurement light beam on the pupil Ep of the eye E to be measured, with respect to the optical axis of the objective lens 2, the follow equation holds true:

$$\tan \delta' / \tan 2\delta = n/n' \quad (6).$$

If (xb, yb) represents the coordinates of the measurement point and r represents the distance from the coordinates (0, 0) of the optical axis of the objective lens 2 on the fundus Ea to the coordinates (xb, yb) of the measurement point, the following equations (7), (8), and (9) are established from equation (6):

$$r = fe \cdot \tan \delta = (n/n') fe \cdot \tan 2\delta \quad (7)$$

$$xb = r \cdot \cos \gamma = (n/n') fe \cdot \tan \delta \cdot \cos \gamma \quad (8)$$

$$yb = r \cdot \sin \gamma = (n/n') fe \cdot \tan \delta \cdot \sin \gamma \quad (9).$$

where γ represents the angle made between the measurement point (xb, yb) and the x axis on the fundus, and the angle of rotation of the image rotator 21. Its counterclockwise direction is a positive direction.

From equations (4), (5), (8) and (9), the position of the measurement point with respect to the center of the macula in the eye E (the position of the fixation target F in the fundus) is determined by the angle information of the image rotator 21 and galvanometric mirror 22 and the position information of the fixation target F.

In this embodiment, the system control circuit 60 computes the measurement point, and the display means 62 presents, at the same time, the position of the measurement point placed at the fixation target F on the fundus and the direction of the extension of the blood vessel Ev determined by the angle of rotation of the image rotator 21.

The angle ψ made by the line connecting the coordinates (xa, ya) of the optical axis of the objective lens 2 on the fundus and the coordinates (xb, yb) of the measurement point and the line connecting the coordinates (0, 0) of the optical axis of the objective lens 2 on the fundus Ea and the measurement point (xb, yb) is determined as follows:

$$\cos \psi = \{r - (xa \cdot \cos \gamma + ya \cdot \sin \gamma)\} / \{(xa - r \cdot \cos \gamma)^2 + (ya - r \cdot \sin \gamma)^2\}^{1/2} \quad (10).$$

If L represents the distance between the coordinates (xa, ya) of the optical axis on the retina and the measurement point (xb, yb), the following equation holds true:

$$L = \{(xa - xb)^2 + (ya - yb)^2\}^{1/2} \quad (11).$$

From equations (4), (5), (8), (9), (10), and (11), each of ψ and L is a function of γ, δ and (X0, Y0).

Figure 13:
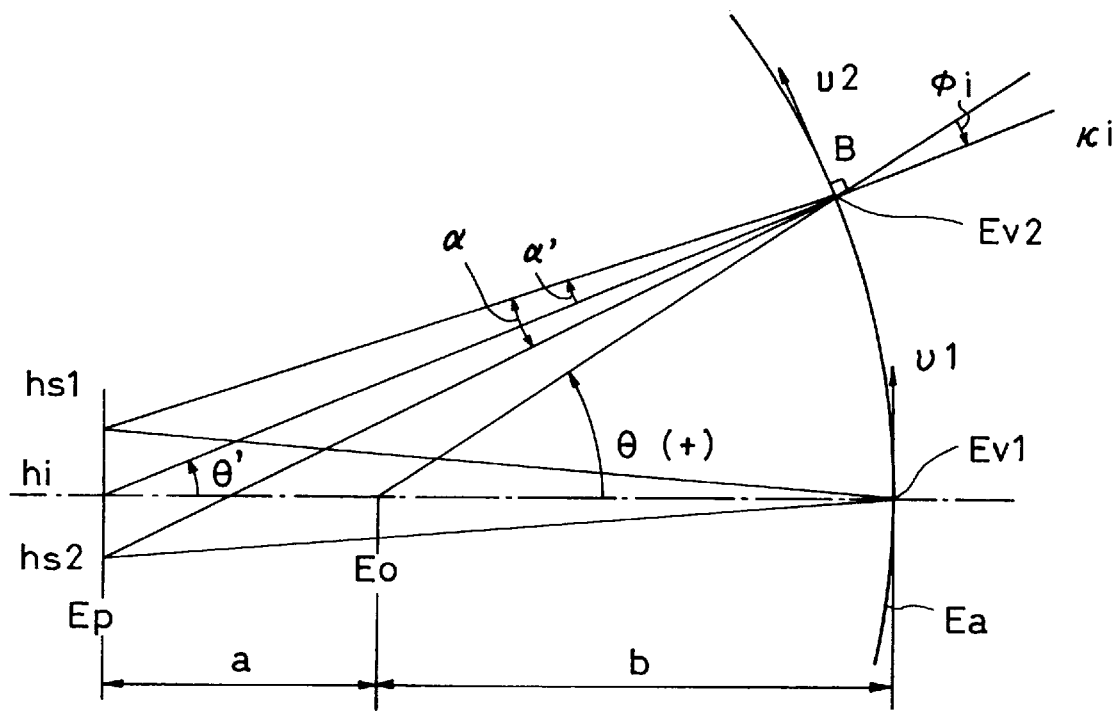
FIG. 13 is an explanatory view showing the sign inversion of a maximum frequency shift.

Now the measurement of a blood vessel having ψ at 90°, namely running radially in the fundus is considered. With the same region of measurement (angle of view), the angle φi between the normal to a blood vessel Ev2 to be measured and the direction κi of the measurement received light is maximized. In FIG. 13, Eo represents the center of curvature of the fundus of the eye to be measured, hs1 and hs2 represent the centers of the measurement received light beams Da and Db, hi represents the center of the pupil of the eye to be measured, φi represents the angle between the normal to the blood vessel Ev2 to be measured and the direction κi of the measurement received light, and a and b represent constants.

As seen from FIG. 13, $$\theta' = \arctan \{b \cdot \sin \theta / (a + b \cdot \cos \theta)\} \quad (12).$$

The angle φi between the normal to a blood vessel Ev2 to be measured and the direction κi of the measurement received light is expressed as follows:

$$\phi i = \arctan \{b \cdot \sin \theta / (a + b \cdot \cos \theta)\} - \theta \quad (13),$$

where θ is easily determined from L in equation (11) and the constant b.

Now the measurement of a blood vessel running concentrically in the fundus is considered. In this case, the optical axis of the objective lens 2, the optical axis of the eye to be measured, and the measurement point are colinear with ψ=0°. With the same region of measurement (angle of view), the angle between the normal to the blood vessel Ev2 to be measured and the direction κi of the measurement received light is minimized, namely 0°.

From the above discussion, the actual angle ωi between the blood vessel Ev2 and the measurement received light direction κi is expressed as follows:

$$\omega i = \phi i \cdot \sin \psi \quad (14)$$

The angle of rotation y of the image rotator 21, the coordinates (X0, Y0) of the fixation target F, and the angle of swing δ of the galvanometric mirror 22 during measurement are recorded. Derived from these data are the angle ψ between the line connecting the coordinates (xa, ya) of the optical axis on the fundus and the measurement point (xb, yb) and the line connecting the coordinates (0, 0) of the objective lens 2 on the fundus Ea and the measurement point (xb, yb), and the distance L between the coordinates (xa, ya) of the optical axis on the fundus and the measurement point (xb, yb). The angle ωi is then determined, and allows one to estimate the area where the signs of the maximum frequency shifts |Δfmax1'|, |Δfmax2'| having the angle ωi as their parameter are inverted and the area where the signs of the maximum frequency shifts |Δfmax1'|, |Δfmax2'| having the angle ωi as their parameter are not inverted. The display means 62 may present ωi to be used to verify the measurement results. The reliability of the measurement results is enhanced.

The signals from the photomultipliers 46a, 46b may be polluted with noise when the eyeball becomes ellipsoidal because of a disease, when the eye suffers a cataract, or when an eyelash interferes. If the maximum frequency shifts |Δfmax1|, |Δfmax2|, |Δfmax1'|, and |fmax2'| computed by the system control circuit 60 are extremely abnormal, the area where the signs of |Δfmax1|, |Δfmax2|, |Δfmax1'|, and |Δfmax2'| are inverted is verified by referring to the angle of rotation γ of the image rotator 21, the coordinates (X0, Y0) of the fixation target F, and the angle of swing δ of the galvanometric mirror 22 during measurement. Such a verification result may be compared to the status of the measurements in the system control circuit 60, and the display means 62 displays an error notice alerts the examiner as shown in FIG. 15.

Although the present invention has been described with respect to the fundus blood flowmeter for measuring the bloodstream velocity in the fundus Ea, the present invention may be applied to an ophthalmological apparatus which measures the position and the diameter of the blood vessel at the same time, besides the bloodstream velocity.

As described above, in the first embodiment, the measurement time is shortened, the dose of light exposure to the fundus of the subject's eyes is reduced and the burden on the subject is lessened by changing the measurement conditions from the artery to the vein. By changing the number of time-series data used in the frequency analysis of the doppler shift signals depending on whether the blood vessel is the artery or the vein, the rise in the bloodstream velocity is faithfully reproduced in the artery measurement, and the frequency resolution is increased in the vein measurement. The measurement accuracy is thus enhanced.

In the second embodiment, by recording the position information of the fixation target image, the image rotator, and the galvanometric mirror during the measurement of the fundus bloodstream velocity of the eye to be measured, the position of the blood vessel measured is determined. The bloodstream measurement featuring a repeatability characteristic serves as data for determining the maximum frequency shift for computing the maximum velocity. The signals may be polluted with noise and correct measurement results may not be obtained when the eyeball becomes extremely ellipsoidal because of a disease, when the eye suffers a cataract, or when an eyelash interferes. In such a case, the exit angles of the measurement light beams are derived from the position information of the fixation target, the image rotator and the galvanometric mirror. The measurement results are then analyzed referring to the exit angles. The examiner can thus easily detect an erratic measurement result.

What is claimed is:

1. An ophthalmological measurement apparatus for measuring bloodstream velocity in a fundus blood vessel in an eye to be measured, said apparatus comprising:
   a measurement system for measuring the bloodstream velocity in said fundus blood vessel;
   an input device for inputting identifying information indicating whether said fundus blood vessel is an artery or a vein; and
   a controller for setting a different measurement time of the measurement system for the artery than for the vein in accordance with the identifying information input by said input device.

2. An ophthalmological measurement apparatus according to claim 1, wherein said controller controls said measurement system to perform a frequency analysis to determine the bloodstream velocity, whose frequency resolution for a vein is higher than for an artery.

3. An opthalmological measurement apparatus according to claim 1, wherein said measurement system uses frequency analysis to determine the bloodstream velocity, wherein said controller further controls said apparatus to prevent velocity variations of interest to an examiner using said apparatus from being obscured by selecting the quantity of data used for the frequency analysis by said measurement system to determine the bloodstream velocity in an artery to be less than the quantity of data used for frequency analysis by said measurement system to determine the bloodstream velocity in a vein.

4. An ophthalmological measurement apparatus for acquiring information relating to an eye of a patient to be measured, said apparatus comprising:
   a fixation target system for generating a fixation target visible to the patient and on which the patient's eye is fixated, wherein said fixation target is movable to guide the patient's eye so that a desired portion of the patient's eye is positioned in a position to be examined by an examiner, the desired portion of the patient's eye including a position of interest on the patient's eye to the examiner;
   a beam directing optical system for directing a beam to the fundus of said eye, wherein said beam directing optical system comprises a beam deflection member for deflecting said beam to the position of interest to the examiner;
   a first detection system for acquiring positional information of said fixation target; and a
   second detection system for acquiring the information relating to the exit angle of said beam by said beam deflection member.

5. An ophthalmological measurement apparatus according to claim 4, wherein said beam deflection member comprises a rotatable mirror arranged at a position approximately conjugate with the pupil of said eye, and
   wherein said second detection system acquires at least the angle information of said rotatable mirror as the information relating to said exit angle of said beam.

6. An ophthalmological measurement apparatus according to claim 4, wherein said beam deflection member comprises an image rotator, and
   wherein said second detection system acquires at least the angle of rotation information of said image rotator as the information of said exit angle of said beam.

7. An ophthalmological measurement apparatus according to claim 4 further comprising a circuit for computing the position of said beam on the fundus of said eye based on said information acquired by said first and second detection systems.

8. An ophthalmological measurement apparatus according to claim 7 further comprising a display for displaying said beam position on said fundus computed by said circuit.

9. An ophthalmological measurement apparatus according to claim 4 further comprising a light receiving system for receiving a light reflected from said fundus of said eye in response to the directed beam and a measurement system for computing said information relating to said eye, based on the received light by said light receiving system.

10. An ophthalmological measurement apparatus according to claim 9 further comprising a memory block for storing said information relating to said eye from said measurement system, said information acquired by said first and second detection systems, or said beam position on said fundus of said eye computed based on said information acquired by said first and second systems.

11. An ophthalmological measurement apparatus according to claim 9, wherein said measurement system estimates the exit angle of said beam from said fundus of said eye based on said information acquired by said first and second detection systems.

12. An ophthalmological measurement apparatus according to claim 4,
   wherein the beam deflection member comprises a rotatable mirror arranged at a position approximately conjugate with the pupil of said eye and an image rotator; and wherein said second detection system acquires at least the angle information of said rotatable mirror and the angle of rotation information of said image rotator as said information relating to the exit angle of said beam and comprises:

a light receiving system for receiving a light reflected from said fundus of said eye in response to the directed beam; a measurement system for computing said information relating to said eye, based on the received light information at said light receiving system; and display means for displaying said information acquired by said first and second detection systems.

13. An ophthalmological measurement apparatus according to claim 12, wherein said measurement system estimates information relating said exit angle of said beam at said fundus of said eye with respect to a line defined by the angle of rotation of the image rotator, based on said information acquired by said first and second detection systems.

14. An ophthalmological measurement apparatus according to claim 13, wherein said directed beam is a coherent beam and said information relating to said eye is the velocity of a bloodstream running in the fundus blood vessel.

15. An ophthalmological measurement method for measuring bloodstream velocity in a fundus blood vessel in an eye of a patient to be measured, said method comprising the steps of:

generating a fixation target visible to the patient, said fixation target being movable to guide the eye so that a desired portion on the fundus of the eye can be observed by an observing system;

directing a beam to the fundus of said eye via a deflection member in order to irradiate the desired protion on the fundus with the beam; and indicating positional information of said fixation target on the fundus and positional information of said beam deflected by said deflection member on the fundus.

16. A method according to claim 15, further comprising the step of indicating the fixation target and the beam with a fundus image on a display.

17. A method according to claim 15, wherein the observing system has an image plane conjugate with the fundus, and wherein said method further comprises the step of imaging the beam and the fixation target on the image plane.

18. An ophthalmological measurement apparatus for acquiring information relating to an eye of a patient to be measured by an examiner, said apparatus comprising:

a fixation target generating member for generating a fixation target visible to the patient and on which the patient's eye is fixated, wherein said fixation target is movable, wherein said fixation target generating member comprises means for guiding the patient's eye when the patient is fixated on said fixation target so that a desired portion of the patient's eye is positioned in a position to be examined by the examiner, wherein the desired portion of the patient's eye comprises a position of interest on the patient's eye to the examiner, wherein said fixation target generating member also comprises means for changing the position of interest;

a beam directing optical system for directing a beam to the fundus of said eye, wherein said beam directing optical system comprises a beam deflection member for deflecting said beam to the position of interest to the examiner;

a first detection system for acquiring the position information of said fixation target;

a second detection system for acquiring the information relating to the exit angle of said beam by said beam deflection member;

means for receiving light reflected from the position of interest illuminated by the beam from said beam directing optical system when the position of interest includes a blood vessel, wherein said beam directing optical system directs the beam to the position of interest from a first direction when the fixation target is positioned at a first position, wherein said beam directing optical system directs the beam to the position of interest from a second direction when the fixation target is moved to a second position;

first and second converting means for converting the received light from the blood vessel into signals;

means for computing first and second maximum doppler shift frequencies of the signals from the first and second converting means, respectively, when said beam directing optical system directs the beam at the position of interest from a first direction and for computing third and fourth maximum doppler shift frequencies of the signals from the first and second converting means, respectively, when said beam directing optical system directs the beam at the position of interest from a second direction;

means for determining the area where the first, second, third, and fourth maximum doppler shift frequencies are inverted; and means for verifying the area where the first, second, third, and fourth maximum doppler shift frequencies are inverted by referring to the information acquired by said first and second detection systems.

* * * * *

UNITED STATES PATENT AND TRADEMARK OFFICE
CERTIFICATE OF CORRECTION

PATENT NO. : 6,192,269 B1
DATED : February 20, 2001
INVENTOR(S) : Toshiaki Okumura et al.

It is certified that error appears in the above-identified patent and that said Letters Patent is hereby corrected as shown below:

Title page,
Item [56], References Cited, U.S PATENT DOCUMENTS,
Insert the following:

| | | | | |
|---|---|---|---|---|
| -- 5,640,963 | 06/1993 | Tanaka | 128 | 665 |
| 5,581,348 | 12/1996 | Miura et al. | 356 | 237 |
| 5,489,978 | 02/1996 | Okumura et al. | 356 | 124 --. |

Item [57], ABSTRACT,
Line 2, "an" should read -- a -- (first occurrence).

Column 1,
Line 26, "let" should read -- let $\lambda$ --.
Line 35, "(1)" should read -- (1). --.
Line 54, "direction" should read -- directions --.

Column 3,
Line 55, "a" should read -- an --.

Column 9,
Line 24, "(every about" should read -- (about every --.
Line 27, "every" should read -- about every --.
Line 28, "about" should be deleted.

Column 11,
Line 20, "operational, member" should read -- operational member, --.

Column 12,
Line 54, "represent" should read -- represents --.
Line 59, "Ea" should read -- Ea, --.

Column 13,
Line 34, "(9)." should read -- (9), --.

Column 14,
Line 37, "(14)" should read -- (14). --.
Line 38, "y" should read -- $\gamma$ --.
Line 59, "suffers" should read -- suffers from --.

UNITED STATES PATENT AND TRADEMARK OFFICE
CERTIFICATE OF CORRECTION

PATENT NO. : 6,192,269 B1
DATED : February 20, 2001
INVENTOR(S) : Toshiaki Okumura et al.

It is certified that error appears in the above-identified patent and that said Letters Patent is hereby corrected as shown below:

Column 15,
Line 3, "notice" should read -- notice that --.
Line 31, "suffers" should read -- suffers from --.
Line 57, "opthalmological" should read -- ophthalmological --.

Column 16,
Line 18, "a" should be deleted.
Line 19, "second" should read -- a second --.
Line 36, "claim 4" should read -- claim 4, --
Line 41, "claim 7" should read -- claim 7, --
Line 44, "claim 4" should read -- claim 4, --
Line 50, "claim 9" should read -- claim 9, --

Column 17,
Line 16, "relating" should read -- relating to --.

Signed and Sealed this

Sixteenth Day of April, 2002

Attest:

Attesting Officer

JAMES E. ROGAN
Director of the United States Patent and Trademark Office